United States Patent
Masuda et al.

(10) Patent No.: US 6,755,932 B2
(45) Date of Patent: Jun. 29, 2004

(54) PLASMA PROCESSING SYSTEM AND APPARATUS AND A SAMPLE PROCESSING METHOD

(75) Inventors: Toshio Masuda, Toride (JP); Tatehito Usui, Niihari (JP); Mitsuru Suehiro, Kudamatsu (JP); Hiroshi Kanekiyo, Kudamatsu (JP); Hideyuki Yamamoto, Kudamatsu (JP); Kazue Takahashi, Kudamatsu (JP); Hiromichi Enami, Tachikawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/788,463

(22) Filed: Feb. 21, 2001

(65) Prior Publication Data

US 2001/0015175 A1 Aug. 23, 2001

(30) Foreign Application Priority Data

Feb. 21, 2000 (JP) ........................................ 2000-048933

(51) Int. Cl.⁷ ............................ H05H 1/00; C23C 16/00
(52) U.S. Cl. ............................ 156/345.24; 156/345.25; 156/345.47; 118/712; 118/723 E
(58) Field of Search .................. 156/345.24–345.25, 156/345.47; 118/712–713, 723 E; 216/67; 438/710; 356/445

(56) References Cited

U.S. PATENT DOCUMENTS 4,887,548 A * 12/1989 Urata et al. ................ 118/722
5,045,149 A * 9/1991 Nulty et al. .................. 438/16
5,231,464 A * 7/1993 Ichimura et al. ............ 356/477
5,578,161 A * 11/1996 Auda ............................. 438/9
5,759,424 A * 6/1998 Imatake et al. ............... 216/60
5,851,842 A * 12/1998 Katsumata et al. ............ 438/9
6,042,650 A * 3/2000 Uesugi et al. ............... 118/712
6,261,372 B1 * 7/2001 Shimizu ...................... 118/712

FOREIGN PATENT DOCUMENTS

JP 8-96988 A * 4/1996 ............ H05H/1/46
JP 2000-299362 A * 10/2000 ........... H01L/21/66

* cited by examiner

Primary Examiner—Parviz Hassanzadeh
(74) Attorney, Agent, or Firm—Antonelli, Terry, Stout & Kraus, LLP

(57) ABSTRACT

The object of the present invention is to provide a plasma processing apparatus wherein plasma is generated in process chamber to treat a sample. Said plasma processing apparatus is further characterized in that multiple closely packed through-holes are formed on the plate installed on the UHF antenna arranged opposite to the sample, an optical transmitter is installed almost in contact with the back of the through-holes, and an optical transmission means is arranged on the other end of said optical transmitter, thereby measuring optical information coming from the sample and plasma through optical transmitter and optical transmission means by means of a measuring instrument. No abnormal discharge or particle contamination occur to through-holes even in long-term discharge process, and no deterioration occurs to the optical performance at the end face of the optical transmitter. Said plasma processing apparatus ensures stable and high precision measurement of the state of the surface of sample and plasma for a long time.

11 Claims, 9 Drawing Sheets

PLASMA PROCESSING SYSTEM AND APPARATUS AND A SAMPLE PROCESSING METHOD

BACKGROUND OF THE INVENTION

1. Field of the Invention

The present invention relates to a plasma processing system and a sample processing method, and particularly to a plasma processing system and sample processing method suited for forming a fine pattern in the semiconductor production process. It relates more particularly to an apparatus or a sample processing method to measure plasma emission in a process chamber and the state of thin film on the surface of such a sample as wafer.

2. Related Background Art

A plasma processing apparatus is extensively used in the fine working phase such as etching, film formation and ashing of the semiconductor production process. In the plasma processing apparatus, the process gas introduced into a vacuum chamber (reactor) is converted into plasma by a plasma generating means, and is made to react on the surface of a semiconductor wafer to provide such treatment as processing of fine holes and grooves or film formation. Furthermore, the required treatment is provided by discharging volatile reaction products.

In this plasma processing apparatus, attempts have been made to detect the end point of the etching process by detecting the radiation from plasma during processing, and to measure the film thickness and etching/film forming rate from the reflective light and interference signal on the thin film of wafer surface for plasma radiation in real time, thereby improving the plasma processing accuracy. For example, Official Gazette of Japanese Patent Laid-Open NO. 136098/1993 discloses a parallel plate plasma etching system where two or more plasma receiving sensors are installed on the surface of the electrode opposite to the wafer, and uniform plasma density is ensured by obtaining information on the rate, film thickness uniformity and distribution from plasma radiation strength at multiple points of the wafer.

Official Gazette of Japanese Patent Laid-Open NO. 148118/1991 discloses a parallel plate plasma etching system where laser beam is applied to the wafer from the upper position through a top plate electrode, and the volume of etching is measured through the reflected laser beam, thereby detecting the end point. To avoid contamination of the top electrode according to said Gazette, this system has a hole with a diameter of about 10 mm formed on the portion of the quartz-made electrode cover where laser beam passes, and measures the volume of etching with high accuracy without laser beam being damped even if the electrode cover is contaminated; this ensures stable detection of an end point.

The methods described above, however, have the following problems: For monitoring of the state of thin film or the like on the wafer surface, it is preferred to measure from the upper position opposite to the wafer or from the upper position at an angle of about 45°. The plasma processing apparatus which allows measurement in such a manner is restricted in the measurement method and structure. In the microwave ECR method and inductively coupled plasma processing apparatus, for example, a quartz-made transparent window and plate may be installed above the wafer in order to apply microwaves inside the process chamber or to introduce inductive electric field. In this case, the state of the wafer surface can be measured from above. However, in the so-called capacitatively coupled parallel plate plasma processing apparatus, the top electrode opposite to the wafer is made of conductive metal such as aluminum, so it is not structured to allow the surface of the wafer to be directly penetrated. For this reason, measurement of the wafer surface requires a sensor for a plasma radiation to be installed on the surface of the electrode opposite to the wafer, as indicated in the Official Gazette of Japanese Patent Laid-Open NO. 136098/1993. However, reaction products are deposited on the sensor for a plasma radiation according to repeated electric discharges. This makes it very difficult to ensure stable measurement for a long time.

One of the attempts to solve this problem is the method disclosed in the Official Gazette of Japanese Patent Laid-Open NO. 148118/1991. A hole having a diameter of about 10 mm is formed on the measurement portion of the quartz-made electrode cover directly exposed to plasma where laser beam passes, thereby eliminating an adverse effect on measurement, despite the deposit membrane formed on the quartz-made cover surface. However, this method does not ensure stable measurement. To get the specified plasma density required for plasma processing, high-frequency power amounting to several kilowatts of high power is applied to the top electrode. If an about 10 mm-diameter hole is formed on the electrode and electrode cover as disclosed in said Official Gazette, local abnormal discharge will occur to the hole, or plasma will enter the hole, and the top electrode and electrode cover may be damaged. Furthermore, bias is applied to the top electrode, the top electrode will be sputtered by ions in plasma through the hole on the electrode cover. Since the top electrode is made of such a metal as aluminum, it may be damaged or entry of particle contamination may result.

Needless to say, the wafer surface can be measured in principle-from the side wall of the process chamber at a smaller inclination, instead of from the upper position opposite to the wafer. However, an opposite plate type where such a plate as silicon is placed opposite to the sample at a position several tens of millimeters away is often adopted especially in the oxide film etching system, in order to control excessive dissociation of process gas and to improve process reproducibility. In this case, the angle of measuring the wafer has to be about 10° in practice. It is also difficult to ensure satisfactory measuring accuracy. Under these circumstances, it has been hoped that the state of wafer surface can be measured from the top opposite to the wafer in the opposite plate type plasma processing apparatus as well.

With reference to the microwave ECR system and inductively coupled plasma processing apparatus, authors of the present invention have described that wafer surface can be measured from a quartz-made transparent window above the wafer. However, reaction products are deposited on the quartz-made window surface as discharge is repeated, and transmittance is reduced. Conversely, surface is etched and is made rough, so stable measurement for a long time is difficult. For this reason, this system has failed to meet practical requirements.

SUMMARY OF THE INVENTION

The present invention has been made to solve said problems. It is intended to provide a plasma processing apparatus and a sample processing method which ensure stable measurement of the sample surface and plasma state from the external vacuum chamber or the wall state of the vacuum chamber with high accuracy for a long time, without abnormal discharge or occurrence of particle contamination.

Authors of the present invention have studied the above problems from the view point of ensuring practicability and reliability, and have found out the following solutions:

The present invention provides a plasma processing apparatus wherein process gas is supplied into a vacuum chamber, plasma is generated by a plasma generator and a sample placed on a sample bench is processed by said plasma; said plasma processing apparatus further characterized in that an optical reflector is arranged within said vacuum chamber, at least one or more through-holes with depth-to-diameter ratios ranging from 5 up to 100 are formed at a position opposite to said optical reflector of said vacuum chamber, and a means of measuring optical information from the surface state of said optical reflector via said through-hole is provided.

The present invention is characterized in that a plasma processing apparatus wherein process gas is supplied into a vacuum chamber, plasma is generated by a plasma generator and a sample placed on a sample bench is processed by said plasma, provides;

an optical reflector which is arranged within said vacuum chamber, at least one or more through-holes with depth-to-diameter ratios ranging from 5 up to 100 which are formed at a position opposite to an optical reflector of said vacuum chamber and on a structure in contact with said plasma, an optical transmitter which is installed on the back of said through-hole so that one end face thereof will be almost in contact with said structure, an optical transmission means which is laid out on the other end face of said transmitter, and a means of measuring optical information from the surface state of said optical reflector via said optical transmitter and said optical transmission means.

The present invention is further characterized in that the diameter of said through-hole is 0.1 mm to 5 mm, desirably 0.3 mm to 2 mm.

The present invention is still further characterized in that the total of the opening area of said through-hole is made 5 to 50% of the total area of the area in which a plural of said through-holes are formed.

A further characteristic of the present invention is that quartz or sapphire is used as said optical transmitter.

A still further characteristic of the present invention is the structure which enables easy replacement of said optical transmitter by removing one set of holding means and vacuum sealing means which holds said optical transmitter in position, when said vacuum chamber is released to the atmosphere.

The present invention is still further characterized in that a plasma processing apparatus wherein process gas is supplied into a vacuum chamber, plasma is generated by a plasma generator and a sample placed on a sample bench is processed by said plasma, provides;

an optical reflector which is arranged within said vacuum chamber, at least one or more through-holes with depth-to-diameter ratios ranging from 5 up to 100 which are formed at a position opposite to an optical reflector of said vacuum chamber, a means of measuring optical information from the surface state of said optical reflector via said through-hole, and a means of determining whether some foreign substance has generated, based on the variations of said optical information.

The present invention is still further characterized in that a plasma processing apparatus wherein process gas is supplied into a vacuum chamber, plasma is generated by a plasma generator and a sample placed on a sample bench is processed by said plasma, provides;

an optical reflector which is arranged within said vacuum chamber, at least one or more through-holes with depth-to-diameter ratios ranging from 5 up to 100 which are formed at a position opposite to an optical reflector of said vacuum chamber and on a structure in contact with said plasma, a means of measuring optical information from the surface state of said optical reflector via said through-hole, and a means of determining to what extent said structure has been consumed, based on the variations of said optical information.

The present invention is still further characterized in that a sample processing method whereof process gas is supplied into a vacuum chamber, plasma is generated by a plasma generator and a sample placed on a sample bench is processed by said plasma, is performed to process said sample while;

measuring optical information from the surface state of said sample via at least one or more through-holes with depth-to-diameter ratios ranging from 5 up to 100 which are formed on the wall of said vacuum chamber at a position opposite to said sample of said vacuum chamber, and while measuring the state of the thin film on the surface of said sample based on the variations of said optical information.

According to the present invention, the plasma processing apparatus is so designed as to provide an optical reflector which is arranged within the vacuum chamber, at least one or more through-holes with depth-to-diameter ratios (aspect ratio) ranging from 5 up to 100 which are formed at a position of a vacuum chamber opposite to an optical reflector, and a means of measuring optical information from the surface state of said optical reflector via said through-hole. So the plasma processing apparatus cannot reduce light transmission characteristics due to adhesion of reaction productions on the end face of an optical transmitter even if making repeated discharge for a long period of time.

Furthermore, the through-hole diameter is so small and aspect ratio is so large that plasma cannot enter internal through-holes to generate abnormal discharge.

What is more, if the quartz or sapphire having an excellent light transmittance and great resistance against plasma is used as an optical transmitter, deterioration of optical performance due to the damage on the end face of the optical transmitter can be sufficiently reduced, thereby ensuring a stable measurement for a long time.

In addition, sample surface and plasma radiation can be measured with sufficient sensitivity and accuracy by compact arrangement of multiple through-holes with an exposed area ratio of 5 to 50%.

What is more, the down time in wet cleaning of the plasma processing apparatus can be minimized by adoption of the structure permitting easy replacement of an optical transmitter 141. This prevents the availability factor of the plasma processing apparatus from being reduced.

In addition, if reaction productions, causing occurrence of particle contamination, which have accumulated at the periphery of the susceptor or on the sidewall inside the vacuum chamber, peel off from the optical reflector, changing a quantity of light from the optical reflector takes place. So detecting this change enables a warning to be generated for the purpose of prevention of frequent occurrence of particle contamination. This warning leads to decide a proper time of cleaning out the internal plasma processing apparatus, enabling to prevent abnormality from occurring during operation of the plasma processing apparatus.

Furthermore, monitoring a quantity of radiation measured with the through-hole on the plate leads to detect consumption of the plate, enabling to prevent abnormality from occurring during operation of the plasma processing apparatus.

DETAILED DESCRIPTION OF PREFERRED EMBODIMENTS

Figure 1:
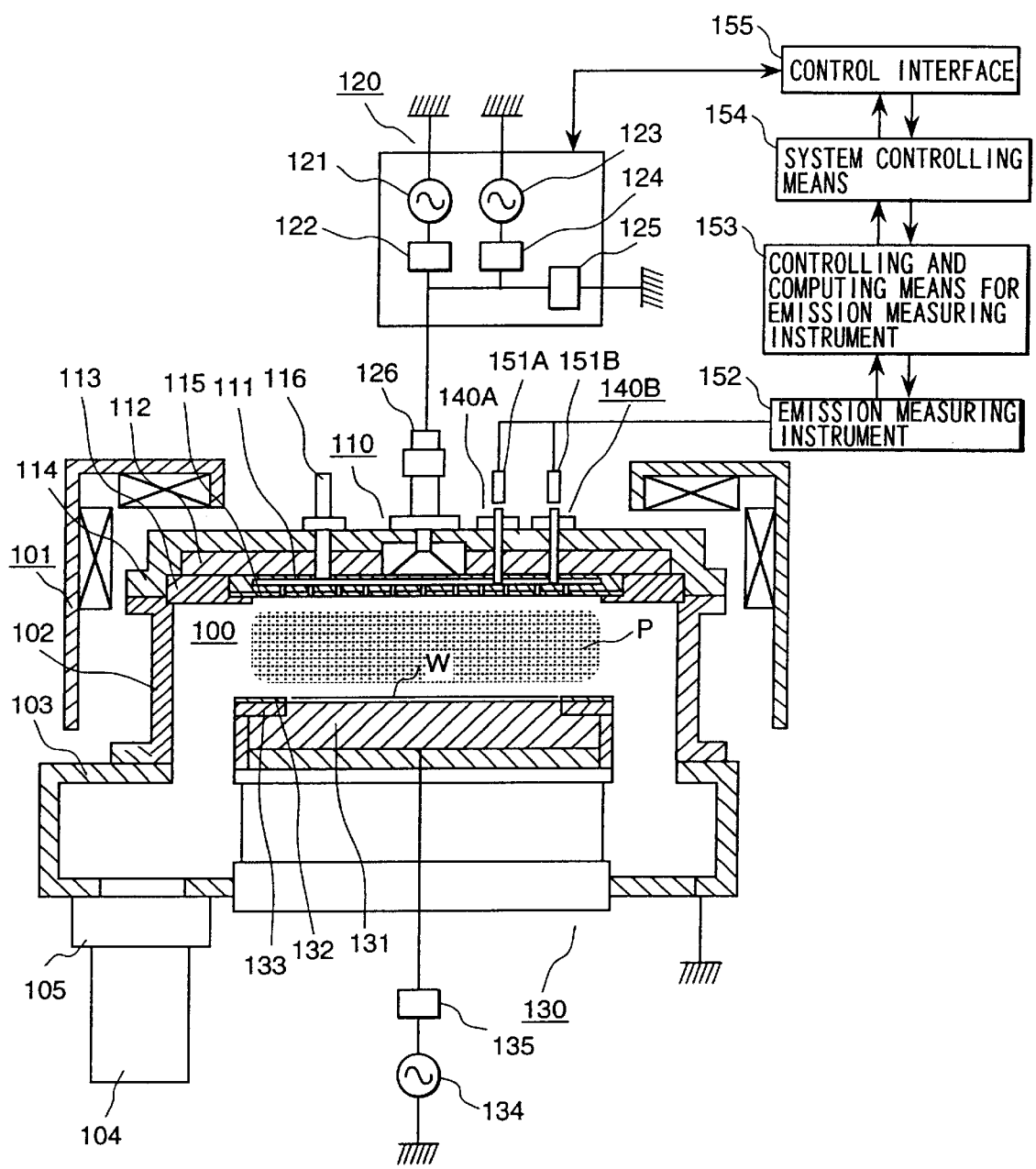
FIG. 1 is a schematic diagram representing the cross section of the plasma etching apparatus as an embodiment of the present invention.

The following describes the embodiments according to the present invention with reference to the drawings:

FIG. 1 shows an embodiment where the present invention is applied to the magnetic field UHF band electromagnetic wave radiation/discharge type plasma etching apparatus. It is a cross sectional view of said plasma etching apparatus in schematic form.

The process chamber 100 in FIG. 1 is a vacuum vessel providing a vacuum of about $10^{-6}$ Torr. An antenna 110 which emits electromagnetic wave as a plasma generating means is provided on the top thereof, and a bottom electrode 130 to mount such sample W as wafer is installed on the bottom thereof. Antenna 110 and bottom electrode 130 are installed in parallel opposite to each other. A magnetic field forming means 101 consisting of an electromagnetic coil and yoke, for example, is installed around the process chamber 100 to provide a magnetic field having a specified distribution and strength. Process gas introduced into the process chamber is made into plasma by interaction between the electromagnetic wave radiated from antenna 110 and magnetic field produced by the magnetic field forming means 101, and plasma P is generated to treat the sample W on the bottom electrode 130.

Vacuum exhaustion and pressure control of process chamber 100 is provided by the vacuum exhaust system 104 connected to vacuum chamber 103 and pressure control means 105, and the internal pressure can be controlled to a specified value, for example, within the range from 0.5 Pa to 4 Pa. The process chamber 100 and vacuum chamber 103 provide ground potential. The side wall 102 of process chamber 100 has its temperature controlled, for example, to 50° C. by a temperature control means (not illustrated).

Antenna 110 radiating electromagnetic waves consists of a disk formed conductor 111, dielectric 112 and dielectric ring 113, and is held by a housing 114 as part of the vacuum vessel. Furthermore, a plate 115 is installed on the surface of the disk formed conductor 111 on the side in contact with plasma. Process gas used to provide sample etching and film formation is supplied at a specified flow-rate and mixing ratio from the gas supply means 116. It is made uniformed inside the disk formed conductor 111 and is supplied to the process chamber 100 through numerous holes provided on plate 115. The temperature of the disk formed conductor 111 is controlled, for example, to 30° C. by a temperature control means (not illustrated). The antenna 110 is connected through the incoming end 126 to antenna power supply system 120 comprising an antenna power supply 121, antenna bias power supply 123 and matching circuit/filter systems 122, 124 and 125. The antenna power supply 121 supplies the UHF frequency power preferably in the range from 300 MHz to 900 MHz to radiate UHF band electromagnetic waves through the antenna 110.

The antenna bias power supply 123 applies to the plate 115 the bias of a frequency of, for example, 100 kHz or several MHz to several tens of MHz through the disk formed conductor 111, thereby controlling the reaction on the surface of plate 115. Especially in the oxide film etching process using CF based gas, reaction of F radical and CFx radical on the surface of the plate 115 can be controlled and the percentage of radicals can be adjusted by using high purity silicon and carbon as the material of plate 115. In the present embodiment, the plate 115 is made of highly pure silicon. Aluminum is used as material for the disk formed conductor 111 and housing, and quartz is used for the dielectric 112 and dielectric ring 113. Distance between the bottom of the plate 115 and wafer W (hereafter called "gap") is 30 mm to 150 mm, or preferably 50 mm to 120 mm. In the present embodiment, the frequency of the antenna power supply 121 is 450 MHz, and that of antenna bias power supply 122 is 13.56 MHz; gap is set at 70 mm.

A bottom electrode 130 is mounted opposite to the antenna 110 on the bottom of the process chamber 100. A sample W such as wafer is mounted on the top surface of the bottom electrode 130, namely, on the sample mounting surface, and is held in position by an electrostatic chucking unit 131. On the peripheral area of the sample W, a sample bench ring 132 made of highly pure silicon, for example, is mounted on the insulator 133. A bias power supply 134 to supply bias electric power preferably in the range from 400 kHz to 13.56 MHz is connected to the bottom electrode 130 through matching circuit/filter system 135, thereby controlling the bias applied to sample W. In the present embodiment, the frequency of the bias power supply 134 is 800 kHz.

The following describes the measuring ports 140A and 140B installed to measure the state of the surface of the sample W as a major portion in the present embodiment. In the present embodiment, measuring ports 140A and 140B are mounted on the antenna 110 opposite to the sample W. As will be described later, the state of thin film on the surface of the sample W can be measured from the top in the vertical direction through numerous through-holes formed on plate 115. Information on distribution inside the surface of the sample W can be obtained by placing the measuring port 140B at the position where the peripheral portion of the sample is measured, and by mounting the measuring port 140A at the position intermediate between the peripheral portion and the center of the sample W. It goes without saying that the position for installation of the measuring port is not restricted to two positions; peripheral and intermediate positions, as described just above. The measuring port can be installed at one position or three positions. Or other arrangement may be used; for example, the port may laid out on the circumference.

For example, optical transmission means 151A and 151B such as the optical fiber and lens are provided on the measuring ports 140A and 140B. Optical information reflecting the surface state of the wafer W such as light directly coming from the plasma P or reflected light or interference light on the wafer W surface of the plasma P is sent, for example, to the camera and interference thin film gauge or measuring instrument 152 consisting of the image processing apparatus, where measurement is performed. The measuring instrument 152 is controlled by the measuring instrument control/operation means 153, and is connected to a higher-order system. The system control means 154 monitors and controls the state of the equipment and system through the control interface 155.

The plasma etching apparatus according to the present embodiment is configured as described above. The following describes a specific process to etch the silicon oxide film, for example, using this plasma etching apparatus:

Firstly, wafer W as an object for treatment is fed into the process chamber 100 from a sample introduction mechanism (not illustrated). It is then mounted and chucked on the bottom electrode 130, and the height of the bottom electrode is adjusted as required. The gap is then adjusted to a specified value. Vacuum-exhausting is made by the vacuum exhaust system 106 inside the process chamber 100. Meanwhile, gases required for sample W etching treatment, for example, $C_4F_8$, Ar and $O_2$ are fed into the process chamber 100 from the plate 115 of the antenna 110 from the gas supply means 116 at a specified flow rate and mixing ratio (for example, Ar at the rate of 400 sccm, $C_4F_8$ at the rate of 15 sccm and $O_2$ at the rate of 5 sccm). At the same time, the pressure inside the process chamber 100 is adjusted to a specified processing pressure: for example, it is adjusted to reach 2 Pa. Meanwhile, almost horizontal magnetic field of approximate 160 gausses corresponding to the electronic cyclotron resonant magnetic field strength for frequency of 450 MHz of the antenna power supply 121 is formed close to the bottom of the plate 115 by the magnetic field forming means 101. The UHF band electromagnetic wave is radiated from the antenna 110 from the antenna power supply 121, and plasma is generated inside the process chamber 100 by interaction with magnetic field. Process gas is dissociated by this plasma P to generate ion and radical. Furthermore, antenna radio frequency power supply 123 and bias power supply 134 are controlled to provide the wafer W with such treatment as etching.

For example, electric power of antenna power supply 121 is 1000 watts, that of antenna radio frequency power supply 123 is 300 watts, and that of the bias power supply 134 is 800 watts. Supply of electric power and process gas is terminated upon termination of etching. Then etching process completely terminates.

The optical information reflecting the state of plasma radiation and wafer surface during this treatment is transmitted by the optical transmission means 151A and 151B through the measuring ports 140A and 140B, and is measured by the measuring instrument 152. The operation is processed by the measuring instrument control/operation means 153 based on the result of measurement. Then the result is transmitted to the high-order system control means 154, and the plasma processing apparatus is controlled through the control interface 155.

Figure 2:
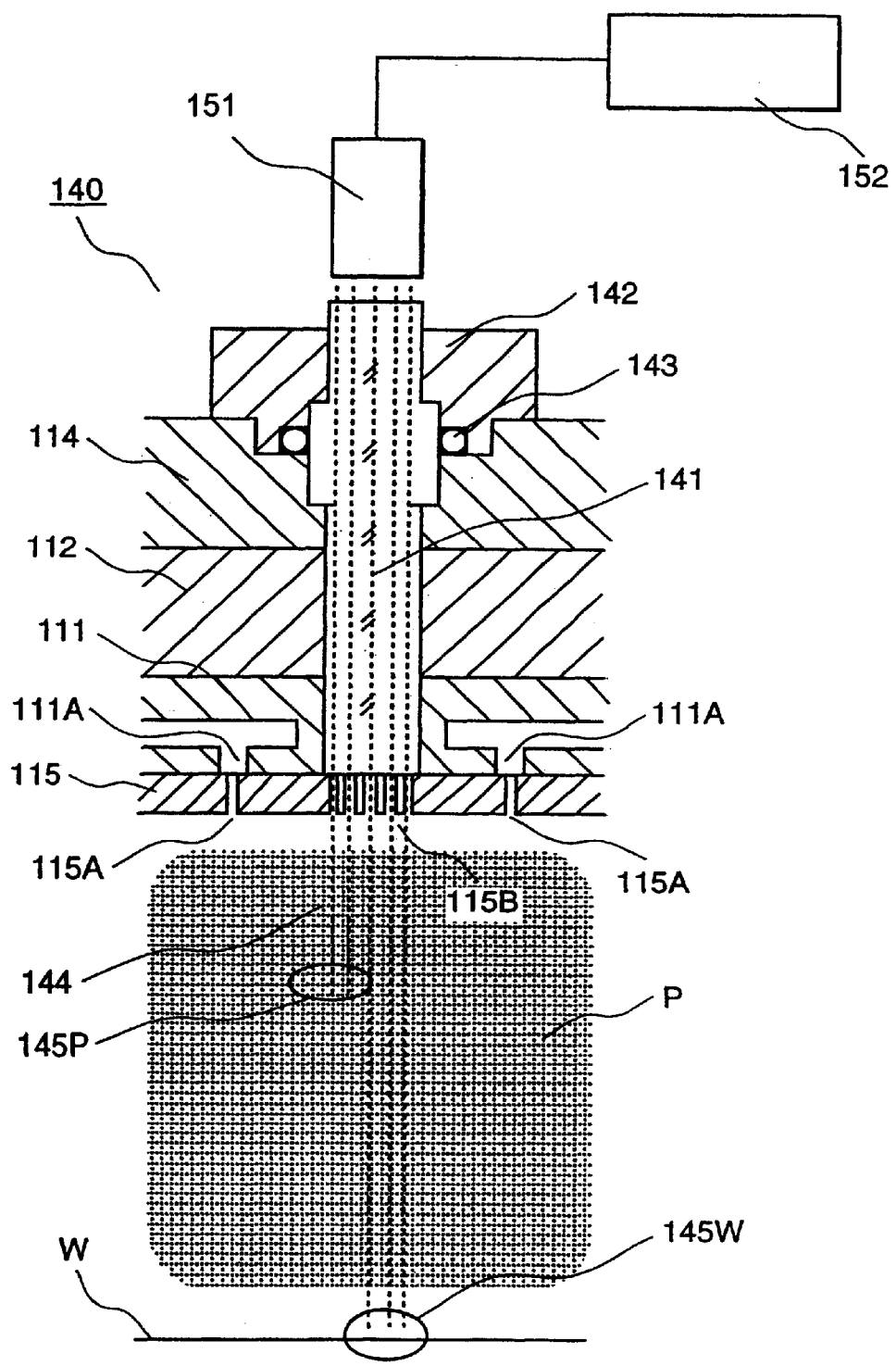
FIG. 2 represents the through-hole section as a major portion of the present invention.
Figure 3:
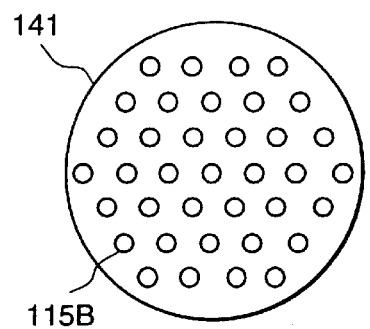
FIG. 3 represents one embodiment of through-hole arrangement according to the present invention.
Figure 4:
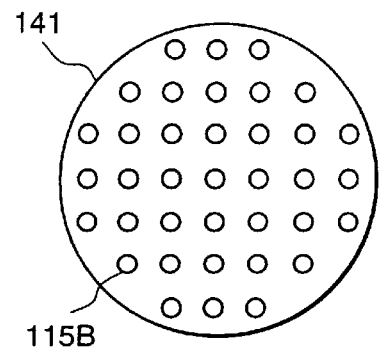
FIG. 4 represents another embodiment of through-hole arrangement according to the present invention.

The following describes the detailed structure of the measuring port 140 with reference to FIGS. 2 to 4:

FIG. 2 is an enlarged cross sectional view representing the portion of the measuring port 140 mounted on the antenna 110 in the embodiment shown in FIG. 1. As described with reference to FIG. 1, the disk formed conductor 111 and dielectric 112 forming the antenna 110 are held by the housing 114, and a plate 115 is installed on the disk formed conductor 111. Numerous gas permeation holes 115A are provided on the plate 115. In the disk formed conductor 111, process gas is fed into the process chamber 100 through gas permeation hole 111A located at the position corresponding to that of gas permeation hole 115A. The gas permeation hole 115A provided on the plate 115, for example, is a through-hole having an approximate diameter of 0.1 mm to 5 mm, preferably, 0.3 mm to 2 mm. The gas permeation hole 111A provided on the disk formed conductor 111 is equal to or greater in size than the hole 115A; for example, it has an approximate of diameter of 0.5 mm to 5 mm, preferably, 2 mm. Approximate thickness of the plate 115 is 3 mm to 20 mm. According to the present embodiment, it is 6 mm.

Numerous closely packed through-holes 115B are formed on the portion of the plate 115 corresponding to measuring port 140, and optical transmitter 141 is installed almost in contact with the back of the plate 115 (on the surface opposite to the plasma P). It is vacuum-sealed with the housing 114 by the holding means 142 and vacuum sealing means 143 such as an O-ring and is mounted in position. Such optical transmission means 151 as an optical fiber and lens, for example, are provided on the end face of the optical transmitter 141 on the atmospheric side. Light 145P directly coming from the plasma P, reflected light from the surface of the sample W of the plasma P, and interference light 145W pass through the through-hole 115B of the plate 115 such as the optical path 144 indicated by a broken line, and reaches the optical transmission means 151 through the optical transmitter 141. They are then sent to the measuring instrument 152, where measurement is performed.

As described later, the aspect ratio of through-hole 115B is preferred to range approximately 5 and more through within 100.

According to this embodiment, the optical transmitter 141 is made of a quartz-made cylindrical rod. The suitable diameter of the optical transmitter 141 is 5 mm to 30 mm. The present embodiment uses a diameter of 10 mm. Similarly to the gas permeation hole 115A, the diameter of the through-hole 115B is 0.1 mm to 5 mm, or preferably 0.3 mm to 2 mm. The diameter of the present embodiment is 0.5 mm. Multiple through-holes 115B, or several tens of them are preferred to be installed to improve the measuring sensitivity. As will be described below, this embodiment uses about 40 holes.

FIG. 3 represents one embodiment of the layout of through-holes 115B. In this embodiment, about 40 through-holes 115B are arranged at a pitch of 1.5 mm in the area corresponding to the end face of the optical transmitter 141 so that a regular triangle is formed at an equally spaced interval. As described above, the diameter of the through-hole 115B is 0.5 mm in this embodiment. The exposed area ratio (percentage of the total apertures of the through-hole 115B for the area of the end face of the optical transmitter 141) is about 10% (=(0.5$^2$ (mm$^2$)×40)/(10$^2$) (mm$^2$)). This can provide a sufficient measuring sensitivity. It goes without saying that the through-hole arrangement is not restricted to FIG. 3 alone. For example, these holes can be laid out so that they will cross one another, as shown in FIG. 4. Or they can be laid out in concentric arrangement. As suggested, holes can be laid out in various arrangements.

Some space (1 mm or more, for example) must be provided between adjacent through-holes. So the exposed area ratio will be reduced as the through-hole diameter is smaller. For example, if holes having a diameter of 0.3 mm are to be laid out at a pitch of 1.3 mm (a width of 1 mm between apertures) in the area having a diameter of 10 mm, the exposed area ratio is about 5%. Measurement is also possible when the exposed area ratio is about 5%. For in-situ measurement of etching rate and others, the exposed area ratio is preferred to be about 5% or more. So from the view point of measurement sensitivity, the through-hole diameter is preferred to be about 0.3 mm or more. Meanwhile, the diameter of the through-hole 115B is preferred to be set sufficiently smaller than the mean free path of the molecule, as will be described later. In order not to allow abnormal discharge to take place, the through-hole diameter is 0.1 mm to around 5 mm, or is preferred to be 0.3 mm to around 2 mm.

If the through-hole 115B diameter is made the same as that of gas permeation hole 115A, there is an advantage that the cost increase can be controlled without increasing the number of processing steps of plate 115. It goes without saying that the hole diameters need not always be made the same. The optimum value can be set according to the sensitivity and stability in measurement. Furthermore, all the diameters of the through-holes 115B need not be made the same. For example, the hole diameter may be larger on the periphery.

The optical transmitter 141 need not be completely "transparent", namely, it need not be transmissive in the entire visible light area. Only a sufficient transmittance is required in the wavelength area to be measured. For example, use of quartz or sapphire is preferred to measure from 200 nm ultraviolet area to 800 nm near-infrared area holding the visible light area in-between. Silicon or such an optical material as ZnS which provides excellent transmittance in the infrared area can be used to measure in the infrared area. Furthermore, a thin film of Al$_2$O$_3$ such as sapphire, for example, may be formed on the end face of the optical transmitter 141 in order to improve resistance to ion sputter and to reduce reflection factor.

The measuring port 140 has the configuration described above. This configuration avoids abnormal discharge, occurrence of particle contamination or deterioration of optical performance such as transmittance at the measuring port 140, and ensures stable measurement for a long time. The following describes the reasons:

If a hole having a diameter of about 10 mm is formed on the top electrode, local abnormal discharge will occur to the hole due to the hollow cathode or plasma will enter the hole to damage the interior, as referred to above as a problem of the prior art. By contrast, the through-hole diameter is set to as small as 0.5 mm in the present embodiment. This does not allow abnormal discharge to occur in the through-hole or the plasma to enter the through-hole. After experiments, the present inventors have verified that measurement can be made without above-mentioned abnormal discharge by setting the diameter of the through-hole 115B to about 5 mm or less, or more preferably to about 2 mm or less. Furthermore, the optical transmitter 141 is installed at the position almost in contact with the back of the through-hole 115B; therefore, there is no space between the through-hole 115B and optical transmitter 141 which may allow abnormal discharge to occur. Thus, abnormal discharge does not occur in this position, either.

The present embodiment ensures stable measurement for a long time without reaction product depositing on the end face of the optical transmitter 141, or transmittance being deteriorated by repeated discharge.

This is because the diameter of the through-hole 115B is set at a value sufficiently smaller than mean free path of molecules, in the first place. Working pressure in the process chamber is about 0.5 Pa to 4 Pa. The mean free path of molecules in this case is about 5 mm to 30 mm (Ar molecule at 25° C.). For this, the diameter $D_h$ of the through-hole 115B is about 0.5 mm, so the ratio with the mean free path of the molecule $\lambda$, namely, the value of $D_h/\lambda$ is about $D_h/\lambda$=0.02 to 0.1. As has been described, the diameter $D_h$ of the through-hole 115B is set at a value sufficiently smaller than the mean free path of the molecule: thus, the possibility is very small that gas molecule in plasma P enters the through-hole 115B.

Secondly, the diameter of the through-hole 115B is 0.5 mm in the present embodiment. By contrast, depth as a plate thickness is set at 6 mm. As described above, the aspect ratio (=depth/diameter) is 10 or more and the hole has a sufficient depth. So the probability of the radical passing through the through-hole 115B and depositing on the end face of the optical transmitter 141 is kept at a sufficient small rate.

Figure 5:
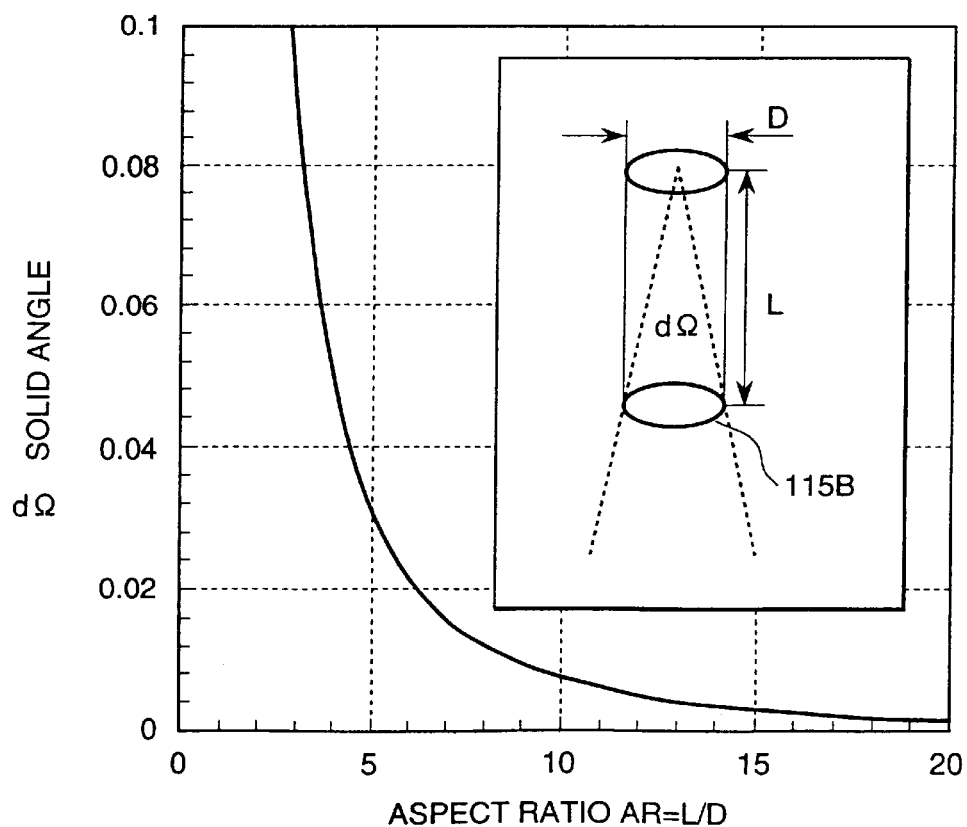
FIG. 5 represents a dependency of the aspect ratio to the solid angle of the through-hole of the present invention.

The possibility of which the radical accumulates on the end face of the optical transmitter 141 is proportional to solid angle dΩ making allowance of the through-hole 115B (hole diameter: D, length: L) on the end face. FIG. 5 shows dependency of the aspect ratio (AR=L/D) of solid angle dΩ. The solid angle dΩ is inversely proportional to the square of AR, as shown in FIG. 5. If the solid angle dΩ is aspect ratios of 5 and more, the solid angle dΩ is below ¹⁄₁₀₀ of solid angleπ on the plane surface. So the possibility of the radical reaching onto the end face of the optical transmitter 141 is kept at a sufficient small rate. In order to get impurity prevention effect on the end face of the optical transmitter 141, the aspect ratio of the through-hole 115B is preferred to range from 5 to 100.

In addition, the plate 115 is heated by plasma, and the surface temperature rises to 100° C. or more. So the possibility of reaction product depositing inside the through-hole 115B is small. Deposits do not attach and grow inside the through-hole 115B to reduce the actual transmission area of the through-hole.

Thirdly, bias voltage of several tens of volts to hundreds of volts is applied to the plate 115; therefore, ion in plasma will be drawn toward the depth of the through-hole 115B. Thus, ion having an energy of several tens of eV to hundreds of eV may reach the end face of the optical transmitter 141, although this probability is low. So even if reaction products have deposited on the end face of the optical transmitter 141, they will be removed quickly by the ion sputtering effect. Optical performance due to damaged end face of the optical transmitter 141 can be reduced sufficiently by manufacturing the optical transmitter 141, for example, with the quartz or sapphire which is highly resistant to plasma.

The following can be said as an overall result of these effects: The optical transmitter 141 does not have reaction products deposited on the end face or the surface roughened, and light transmission is kept constant, despite repeated discharge. This ensures stable measurement for a long time.

Regarding above-mentioned three factors, authors of the present invention have continued experimental studies, and have verified that stable measurement can be made without abnormal discharge by setting the through-hole diameter to 0.5 mm and plate thickness to 6 mm, with respect to the case where the oxide film on the surface of example W is subjected to etching processing, as explained in the present embodiment. FIG. 5 is a schematic diagram of the signal waveforms gained in the present experiment. Interference signals resulting from changes in interference due to light reflected from the oxide film surface and underlying layer are obtained with the progress of etching treatment. In-situ measurement of the etching rate is possible from this cycle. In addition, plasma emission signal as light directly coming from plasma is also gained. These interference signals and plasma emission signals are changed simultaneously at the end point of the etching processing. It is clear that the state of the surface and changes of plasma composition at the end point of the etching processing can be detected. These signals can be detected with sufficiently high precision over at least several tens of hours of discharge. Furthermore, the number of particle contamination having occurred during this time does not exceed 20 (0.2 microns or more). Thus, stable measurement has been confirmed.

As can be seen from FIG. 2, the optical transmitter 141 is held and is vacuum sealed by the holding means 142 and vacuum sealing means 143 alone. This allows easy replacement by removing the holding means 142 when the process chamber is released to the atmosphere. Consequently, if deposits are gradually accumulated on the end face of the optical transmitter 141 or the surface is roughened by ion sputtering, depending on process conditions, then easy replacement of the optical transmitter 141 is possible when wet cleaning is made by releasing the plasma processing apparatus to the atmosphere. This minimizes the down time at the time of wet cleaning (complete cleaning).

Figure 6:
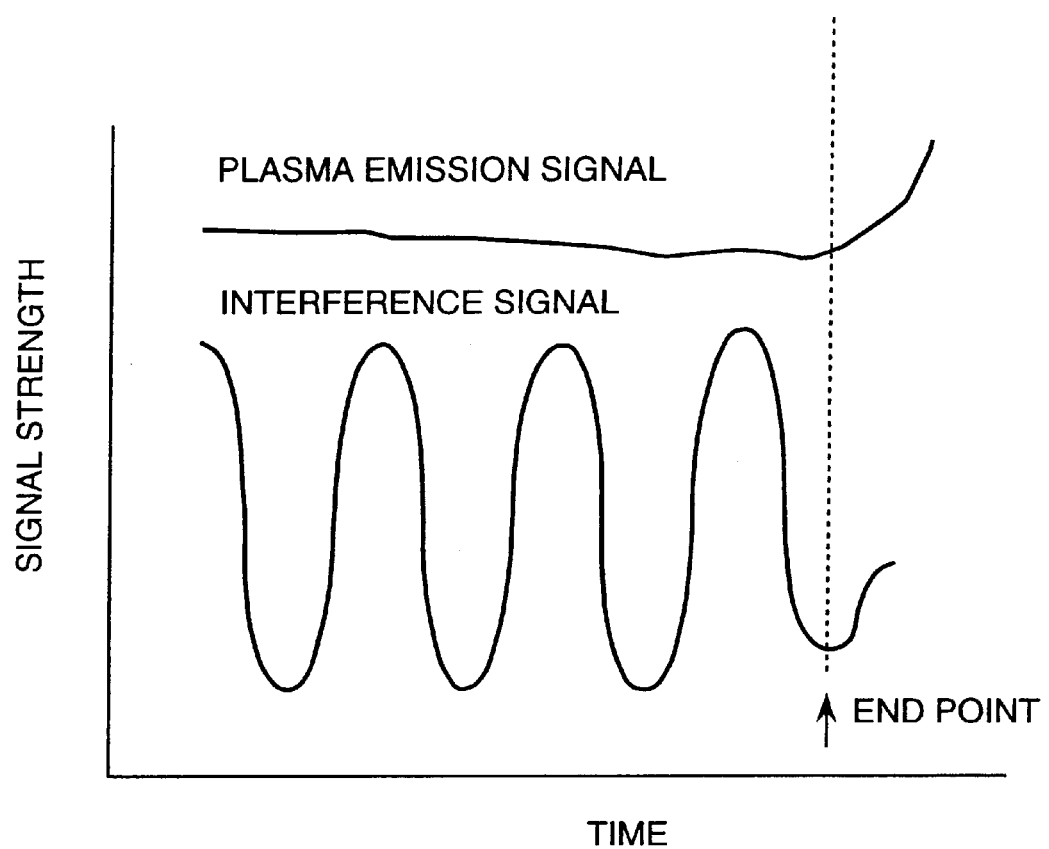
FIG. 6 represents an example of a experimental signal in the embodiment.
Figure 7:
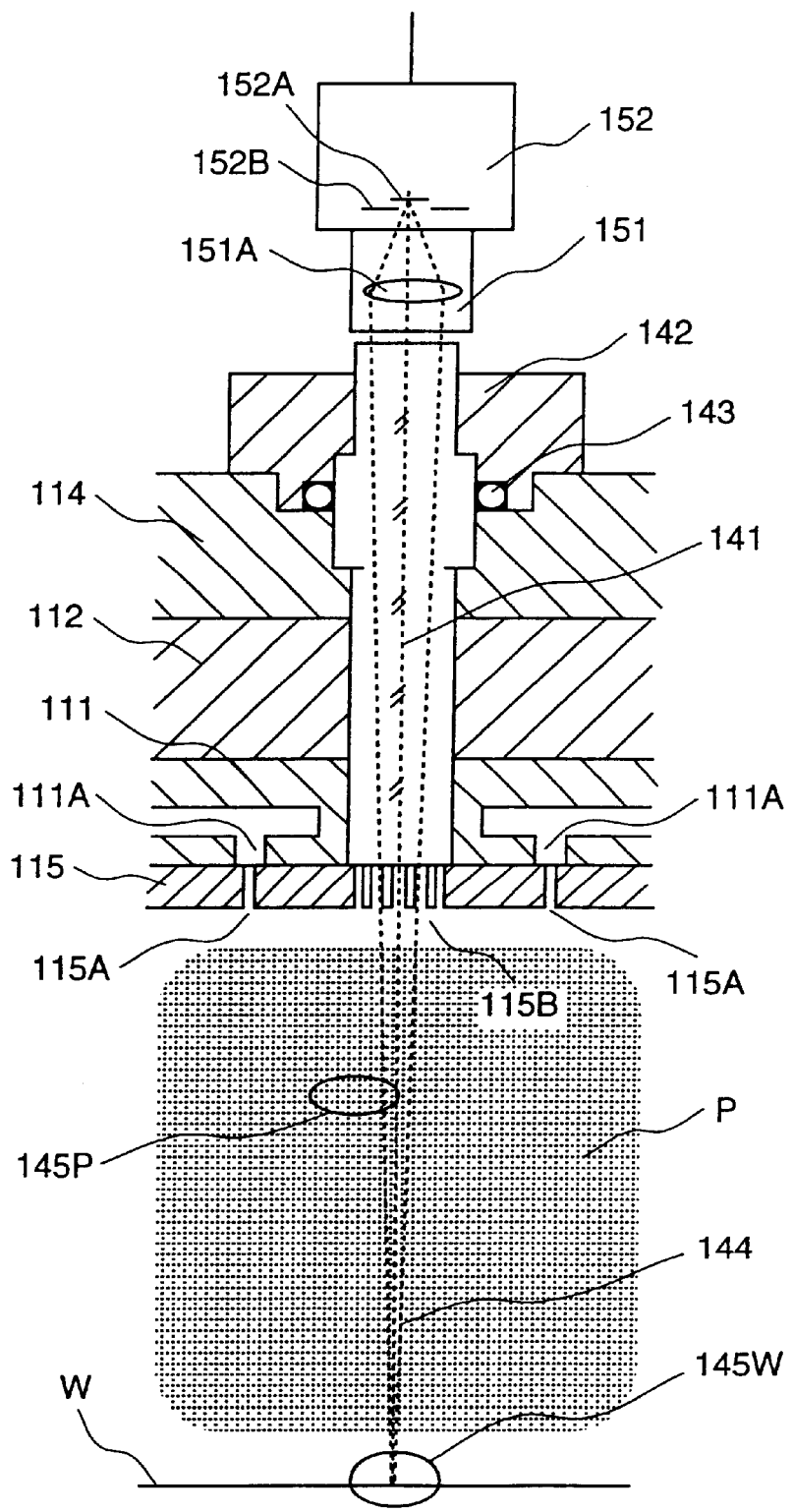
FIG. 7 is a drawing used to explain an example using an image forming optical system as another embodiment according to the present invention.

Using FIGS. 6 and 7, the following describes another embodiment, the detection optical system which provides measurement through the through-hole 115B. In the embodiment shown in FIG. 2, the optical transmission means 151 is made of an optical fiber. Light 145P directly coming from plasma P located in the middle of the optical path 144, and reflected light and interference light 145W on the surface of sample W of plasma P all enter the optical fiber for measurement. Especially when radical components in plasma are changed with the progress of etching processing, this arrangement is suited to detect such a change. Meanwhile, for sensitive detection of the change in the state of surface such as thickness of a thin film of sample W, light directly emitted from plasma P forms a noise component for measurement. So failure of its detection may be preferable to the measuring system. In such cases, an image forming optical system using a lens or the like is preferably used for the optical system.

FIG. 7 shows one embodiment of such an optical system. In the present embodiment, the optical transmission means 151 uses a lens 151A as an image forming means. Optical information from the surface of the sample W is made to form an image on the detecting element 152A of the measuring instrument 152 such as the camera and image processing apparatus. Light 145P directly coming from plasma P is cut off by arranging the filter 152B including the diaphragm and pin hole immediately before the detecting element 152A. Only the optical information 145W from the surface of sample W can be transmitted to the detecting element 152A. This improves the sensitivity of detection and measurement of the state on the surface of sample W.

In the present embodiment, a through-hole 115B is located at some midpoint in the optical system. It may appear difficult to measure the surface of sample W because the optical path is cut off. However, when the aspect ratio (=depth/diameter) of the through-hole 115B is set to an appropriate value in relation to the expansion of light from the surface of sample W, measurement is possible without the through-hole 115B cutting off the optical path.

Figure 8:
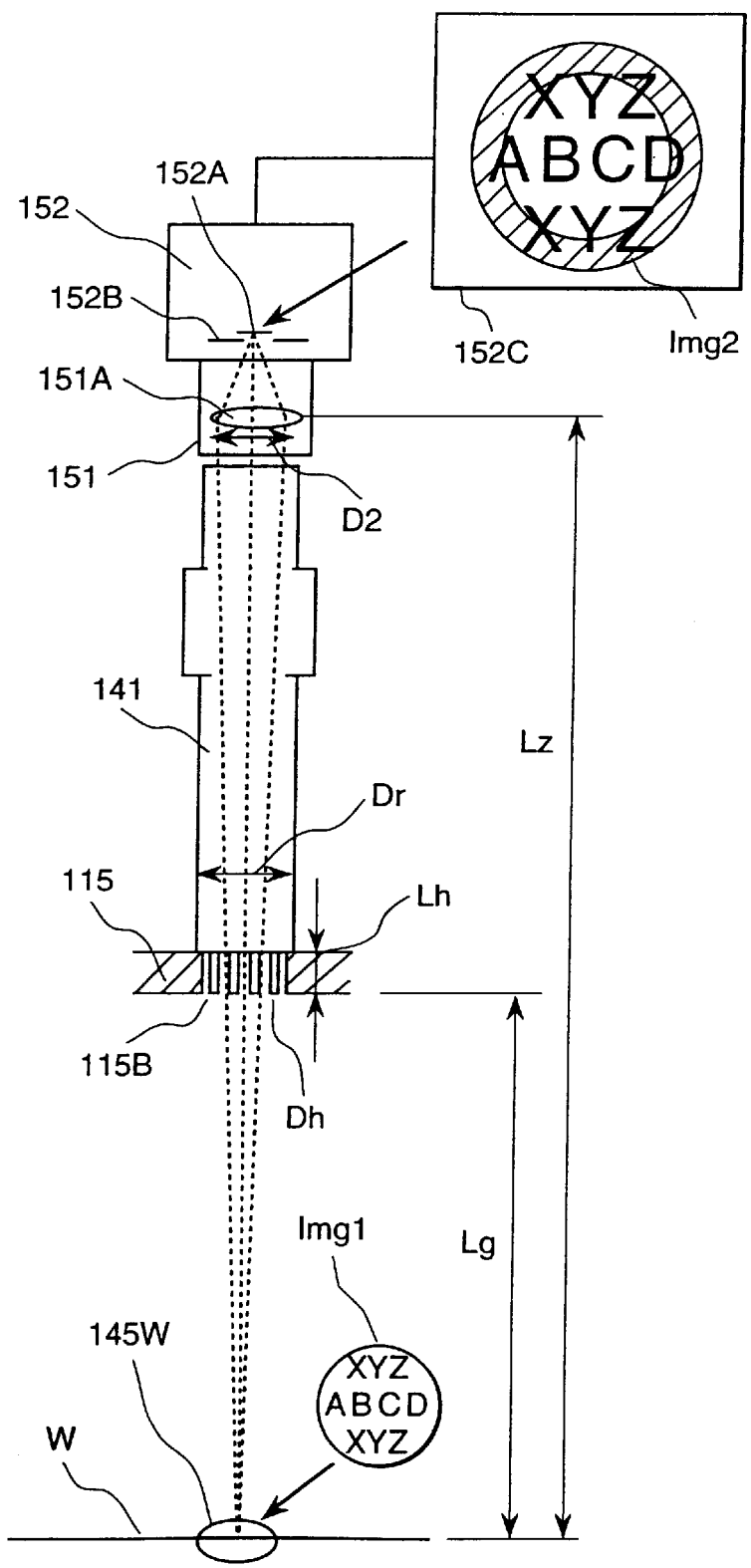
FIG. 8 is a drawing used to explain operations in the embodiment of FIG. 6.

This will be described in greater details with reference to FIG. 8. FIG. 8 is a schematic diagram showing only the portion related to the measurement and optical system of the embodiment shown in FIG. 7. The following shows the symbols in the Figure.

$D_h$: Diameter of through-hole 115B
$L_h$: Depth of through-hole 115B (equal to the thickness of plate 115)
$L_g$: Distance between sample W and plate 115 (equivalent to gap described in embodiment of FIG. 1)
$L_z$: Distance from sample W to image forming means 151A ($L_z-L_g$ is equivalent to thickness of antenna portion described in embodiment of FIG. 1)
$D_z$: Effective diameter of image forming means (lens according to the present embodiment) 151A (almost equivalent to the diameter $D_r$ of optical transmitter 141)

As already described, each of the actual values in the present embodiment is as follows: $D_h$=0.5 mm (diameter), $L_h$=6 mm, $L_g$=70 mm and $D_r=D_z$=10 mm (diameter). Furthermore, the thickness of antenna portion is $L_z-L_g$=80 mm, so $L_z$=150 mm.

Here the divergence angle θ from the surface of sample W is expressed by $θ_z$=tan−1 (($D_z$/2)/$L_z$), based on ratio $L_z/D_z$ between distance $L_z$ of the image forming means 151A from the sample W and effective diameter $D_z$. In the present embodiment, $θ_z$=1.9°. $L_z/D_z$ equivalent to the divergence angle of beam from the surface of sample W is about 15. By contrast, prospective angle $θ_h$ based on the aspect ratio $L_h/D_h$ of the through-hole 115B is defined as $θ_h$=tan−1 (($D_h$/2)/$L_h$); then $θ_h$=2.3°. This value is a little smaller than $θ_z$=1.9°. As described above, if the beam divergence angle $θ_z$ from the surface of sample W is set to a value a little smaller than the prospective angle $θ_h$ of the through-hole 115B, beam from the surface of sample W will reach the image forming means 151A without being cut off by the through-hole 115B, and will form an image on the detecting element 152A.

FIG. 8 shows how this was verified by experiment. Image Img1 of a character of several mm square was depicted on the surface of sample W. The surface of sample W was observed during plasma processing. Then it was found out that Image Img1 was optically transmitted to the surface of sample, and image Img2 is displayed on the display screen 152C of measuring instrument 152. This image Img2 was slightly affected on its periphery by the eclipse resulting from by the through-hole 115B (expressed by the broken line in concentric circle in FIG. 8), but information on the original image Img1 is sufficiently retained. It has a sufficient quality to measure the state of thin film on the surface of sample W. Oxide film of the surface of sample W was subjected to etching processing by plasma P. Then interference signals due to light reflected from the oxide film surface and underlying layer were obtained corresponding to changes in the thickness of oxide film according to the progress of etching treatment, similarly to what was shown in FIG. 6. This experimentally verified that in-situ measurement of the etching rate is possible.

Figure 9:
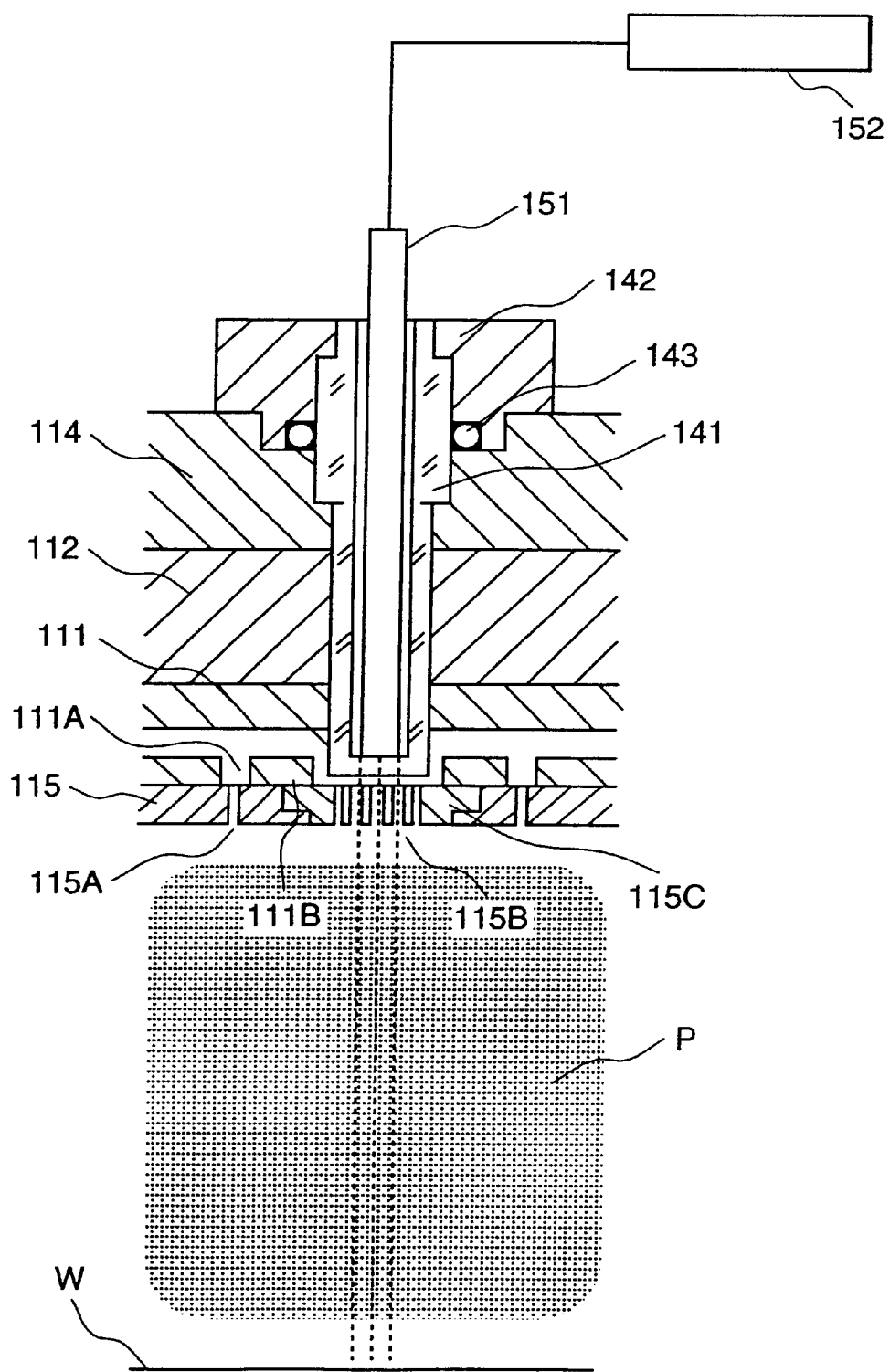
FIG. 9 represents an example of using a hollow structure in the optical transmitter as another embodiment according to the present invention.

Incidentally, the embodiments mentioned above use the optical transmitter 141 made of a quartz-made rod. This is only one example. It goes without saying that other arrangements are also possible. The following describes another embodiment with reference to FIG. 9. FIG. 9 shows the arrangement where the rod as an optical transmitter 141 was made hollow with its interior removed, and an optical fiber was inserted therein as an optical transmission means 151. In FIG. 9, a gas supplier 111B is provided on the portion corresponding to the through-hole 115B of the disk formed conductor 111. So even under the process conditions where reaction products are likely to deposit on the end face of the optical transmitter 141, it is possible to prevent reaction products from depositing since process gas is also supplied from gas supplier 111B. What is more, the optical path for the light passing through the optical transmitter 141 can be shortened as shown in FIG. 9. This has the effect of reducing loss of optical information.

Figure 10:
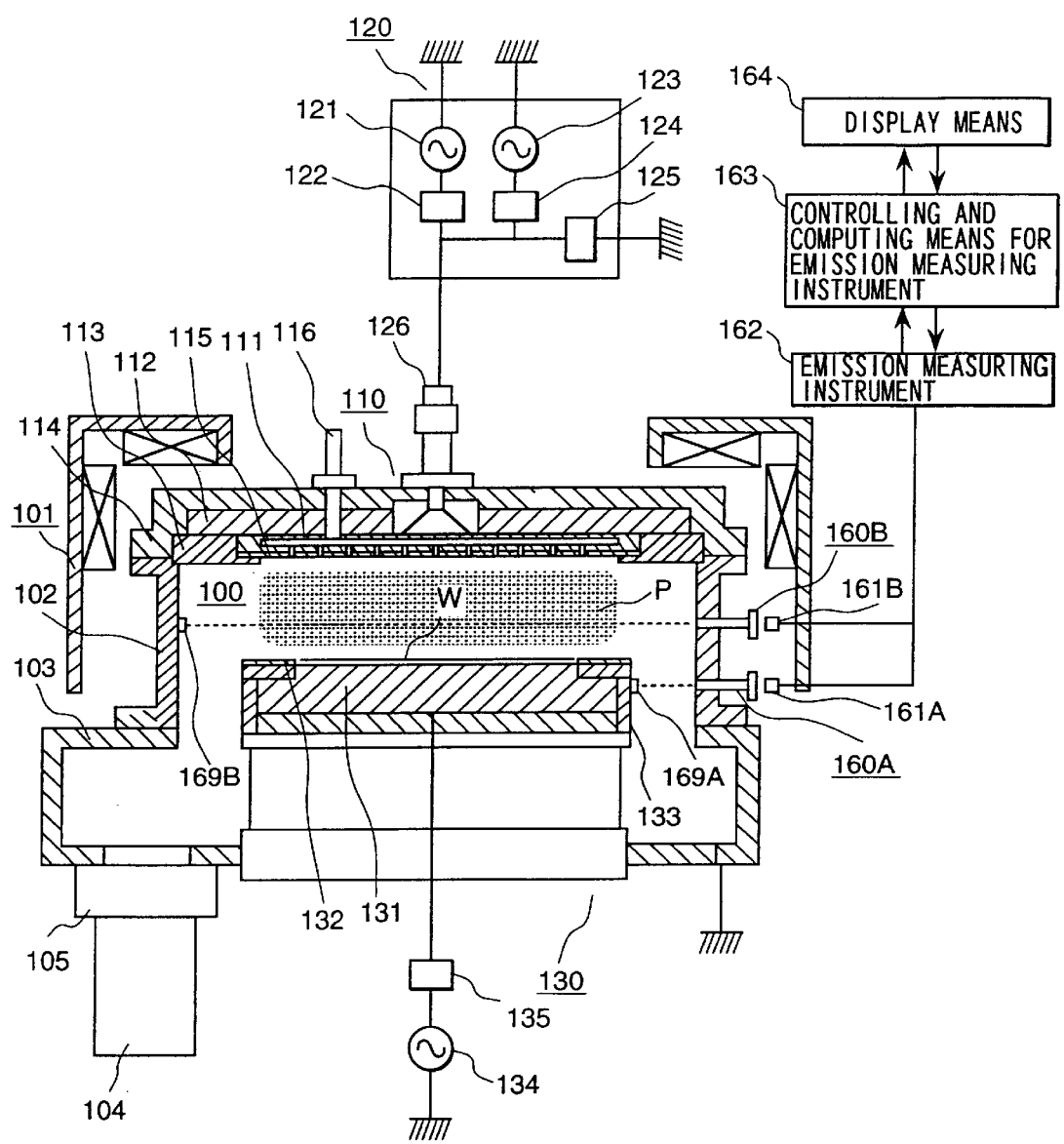
FIG. 10 is a drawing to explain an example of diagnosing the apparatus by installing a reflector on the susceptor or on the sidewall of the vacuum chamber.

Next, description will be made of the embodiment of detecting the change of a quantity of reaction productions, causing the occurrence of particle contamination, accumulating at the periphery of the susceptor and on the sidewall inside the vacuum chamber, with reference to FIG. 10. This description will be omitted of the identical parts to those in FIG. 1. The optical reflectors 169A and 196B are installed on the sidewall of the insulator 133 covering the susceptor or on the sidewall inside the vacuum chamber 102. A measuring port 160A or 161A having the through-hole of the present invention is installed at a position opposite to these reflectors. Measurement is made by transmitting the change of reflected or interfered light from the reflectors to an optical measuring instrument 162 via the optical transmission means 161A or 161B. The optical measuring instrument 162 is controlled by a measuring instrument control means and calculation means 163. When measured amount of reflected or interfered light has changed substantially, a display means 164 issues a warning.

According to this embodiment, if reaction productions, causing occurrence of foreign substance, which have accumulated at the periphery of the susceptor or on the sidewall inside the vacuum chamber, peel off from the optical reflector, changing a quantity of light from the optical reflector takes place. So detecting this change enables a warning to be generated for the purpose of prevention of frequent occurrence of foreign substance. This warning leads to decide a proper time of cleaning out the plasma processing apparatus, enabling to prevent abnormality from occurring during operation of the plasma processing apparatus.

Figure 11:
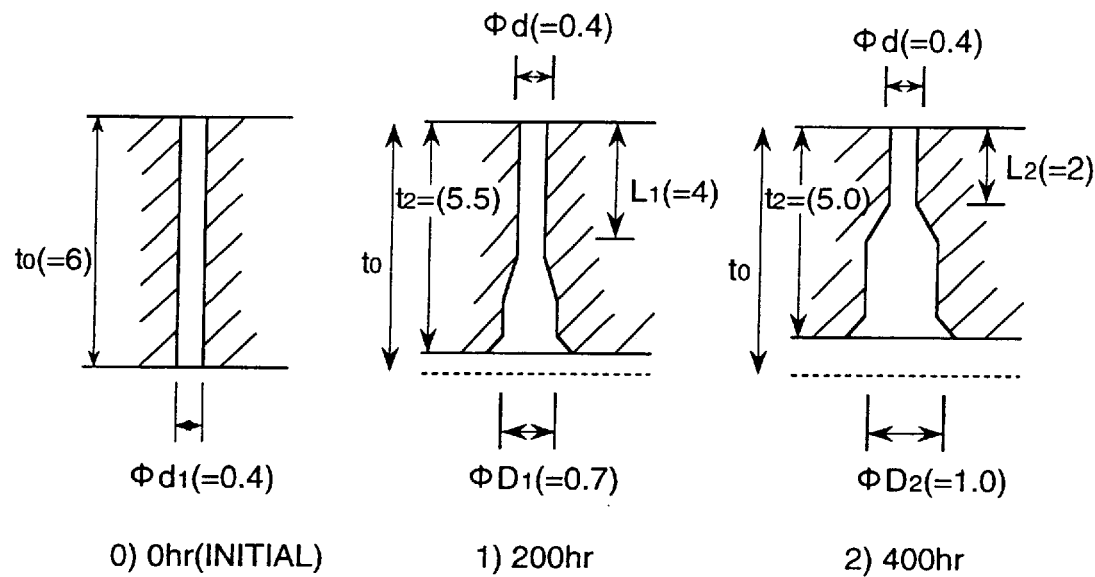
FIG. 11 is a sectional view of a gas effluence port to explain an example of diagnosing the apparatus with respect to consumption detection of the plate for supplying gas in other embodiments of the present invention.

Next, description will be made of the embodiment of detecting consumption of the plate 115 for diagnosing the system during a continuous etching processing, with reference to FIG. 11 and FIG. 12.

High frequency power is applied to the plate 115 through the antenna power supply 121 during wafer-etching processing, so the plate is etched and consumed. FIG. 11 shows the processing-time dependency of the cross section of gas effluence port 115A on the plate 115. As shown in FIG. 11, longer time of etching processing decreases the thickness of the plate and increases the diameter of the hole on the vacuum chamber side. When further etching processing is continued, the gas effluence port 115A becomes a through-hole of approximately 4.5 mm in thickness and of approximately 1.3 mm in hole diameter. Such a gas effluence port increases area by 10.6 times in initial etching processing. So this makes a supply state of etching gas change significantly, makes abnormal discharge induce in the gas effluence port, or makes occurrence of foreign substance more possible, causing a serious damage to continuous etching processing.

Figure 12:
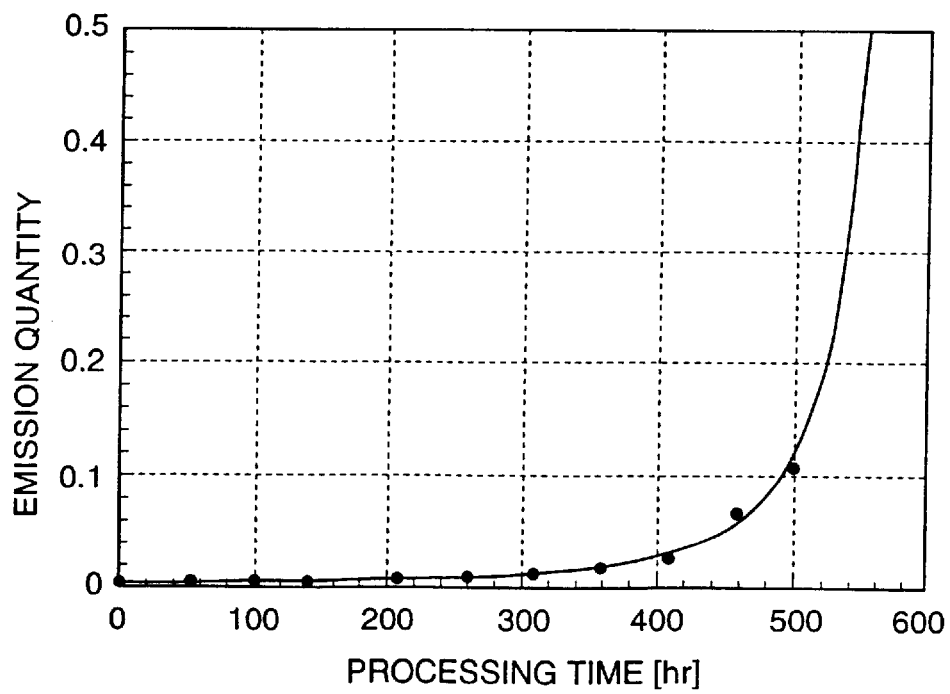
FIG. 12 is a drawing to explain the changes in emission and solid angle in the embodiment of FIG. 11.

In FIG. 12, the solid line represents changes in solid angle $d\Omega$, which are disposed under the shape of gas effluence port. In addition, the changes in a quantity of radiation at this time are given by marking some black circles. FIG. 12 shows that a solid angle $d\Omega$ does not indicates a great change within 400 hours of processing time, but it increases rapidly when processing time exceeds 500 hours. It is also found that the changes in a quantity of radiation has a similar tendency. This proves that, when processing time exceeds 500 hours, this makes more possible occurrence of a serious damage to continuous etching processing.

According to this embodiment, monitoring a quantity of radiation measured through a measuring port with the through-hole of the present invention detects consumption of plate 115, enabling to prevent abnormality from occurring during operation of the plasma processing apparatus.

All of said embodiments have referred to the magnetic field UHF band electromagnetic wave radiation/discharge type plasma processing apparatus. However, for example, 2.45 GHz microwave or VHF band wave ranging from several tens of MHz to 300 MHz in addition to the UHF band wave can be radiated as electromagnetic wave. Magnetic field strength has been explained for the case of 160 gausses which signify electronic cyclotron resonant magnetic field strength for 450 MHz. The resonant magnetic field need not necessarily be used; a stronger magnetic field or weak magnetic field on the order of several tens of gausses or more may be used. Furthermore, it goes without saying that the present invention can also be applied to capacitatively coupled parallel plate plasma processing apparatus and magnetron type plasma processing apparatus or inductively coupled plasma processing apparatus, in addition to electromagnetic wave radiation/discharge type plasma processing apparatus.

The structure of the upper plate opposite to the wafer is comparatively simple especially in the plasma processing apparatus where radio frequency is applied to the bottom electrode and a ground plate is mounted on the top. This makes it easy to install a measuring port similar to that of the present invention. Furthermore, in the parallel plate plasma processing apparatus where radio frequency is applied to the top electrode to generate plasma, several kilowatts of high power radio frequency is applied to the top electrode. So abnormal discharge can occur if a hole or void is provided on the top electrode. According to the structure of the present invention, however, abnormal discharge or other failure does occur to the measuring port. Especially in the narrow electrode type parallel plate plasma system, the space between the top and bottom electrodes is small, and so it is very difficult to get from the side the information on the wafer surface and the plasma between top and bottom electrodes. This indicates that the present invention provides considerable advantages.

Meanwhile, in the inductively coupled plasma processing apparatus (ICP), the state of wafer surface can be measured to some extent when a transparent quartz is used for the top plate. The measuring port according to the present invention can be applied when an alumina-made dome and silicon plate or the like is used. To put it more specifically, those skilled in the art can easily design the arrangement where multiple closely packed holes are formed on an alumina-made plate or the like as shown in FIG. 3, and a vacuum sealing quartz plate is installed on the back. In the ICP type plasma processing apparatus, the top plate may have to be heated to a high temperature of 150° C. or more, for example, in order to get the process characteristic and reproducibility. It goes without saying that the present invention is applicable even under such temperature conditions.

The object to be treated was a semiconductor wafer in each of said embodiments, and etching of the semiconductor wafer was mentioned. However, the present invention is not restricted to them. For example, the present invention is also applicable when the object for treatment is a liquid crystal substrate. In addition, treatment is not restricted only to etching. For example, the present invention is also applicable to sputtering and CVD treatment.

As described above, the present invention ensures a stable and a long-term measurement of the state of the sample surface and plasma or the state of the wall of the vacuum chamber with high accuracy from the external vacuum chamber, without allowing abnormal discharge or particle contamination to occur.

For example, the present invention ensures a stable and precision measurement of the state of thin film of the plasma and sample surface from above the sample W or from the upwardly inclined position for a long time even on a mass production level, in the opposite plate type structure where the antenna and electrode are installed opposite to the wafer surface, without allowing abnormal discharge or particle contamination to occur. As a result, it enables detection of the end point in etching process and in-situ monitoring of etching/film forming rate and uniformity. Thus, the present invention permits a more advanced process control and improves reproducibility of treatment and stability in treatment, and provides a plasma processing apparatus contributing to improvement of the apparatus availability factor and productivity.

What is claimed is:

1. A plasma processing apparatus comprising:
   a sample bench located in a vacuum chamber;
   a conductive plate member coupled to a power source and disposed opposed to a sample placed on the sample bench for radiating electromagnetic waves into the vacuum chamber, in which a gas is supplied into the vacuum chamber to generate a plasma and to process the sample with the plasma, the conductive plate member having at least one through hole therein with an opening on a side facing the generated plasma at a position opposed to the sample, at least one through hole having a depth-to-diameter ratio ranging from 5 to 100;
   an optical transmitter mounted with respect to the vacuum chamber so as to be substantially in contact with a back of the at least one through hole in the conductive plate member, the back of the at least one through hole being disposed opposite to the opening of the at least one through hole in the conductive plate member on the side facing the generated plasma; and
   means for measuring the light from the sample passing through the at least one through hole by way of the optical transmitter.

2. A plasma processing apparatus according to claim 1, wherein the light from the sample contains optical information showing a surface state of the sample.

3. A plasma processing apparatus according to claim 1, wherein a total of an area for the opening of the at least one through hole ranges from 5% to 50% of a region of the conductive member which is covered by an end face of the optical transmitter.

4. A plasma processing apparatus comprising a sample bench located in a vacuum chamber;
   an antenna coupled to a power source and disposed opposed to a sample placed on the sample bench, the antenna having at least one through hole in a portion thereof with an opening of the at least one through hole provided at a position opposed to the sample on the side of the antenna facing a plasma generated in the vacuum chamber, the at least one through-hole having a depth-to-diameter ratio ranging from 5 to 100;
   an optical transmitter mounted to the antenna and disposed so as to be substantially in contact with a back of the at least one through hole which is disposed opposite to the opening of the at least one through hole on the side facing the generated plasma; and
   means for measuring a light from the sample passing through the at least one through hole by way of the optical transmitter.

5. A plasma processing apparatus according to claim 4, wherein the light from the sample contains optical information showing a surface state of the sample.

6. A plasma processing apparatus according to claim 4, wherein a total of an area for the opening of the at least one through hole ranges from 5% to 50% of a region of the antenna which is covered by an end face of the optical transmitter.

7. A plasma processing apparatus comprising a sample bench located in a vacuum chamber, and a conductive plate member coupled to a power source and mounted opposed to the sample placed on the sample bench for radiating electromagnetic waves into the vacuum chamber and in which a gas is supplied into the vacuum chamber to generate a plasma and to process the sample by the plasma, the plasma processing apparatus further comprising:
   at least one through hole formed in the conductive plate member and having an opening on a side facing the generated plasma and disposed at a position opposed to the sample, the at least one through hole having a depth-to-diameter ratio ranging from 5 to 100;
   an optical transmitter disposed with respect to the vacuum chamber so as to be substantially in contact with a back of the at least one through hole which is opposite to the opening in the conductive plate member on the side facing the generated plasma;
   means for measuring a light from the sample that passes through the at least one through hole by way of the optical transmitter, thereby detecting optical information showing a surface state of the sample; and
   means for judging the state of generation of obstacles in the processing chamber based on the fluctuation of the optical information.

8. A plasma processing apparatus, comprising a sample bench located in a vacuum chamber, an antenna disposed opposed to a the sample placed on the sample bench, at least one through hole formed in a portion of the antenna and having an opening at a position opposed to the sample on the side of the antenna facing the plasma generated in the vacuum chamber, the at least one through hole having a depth-to-diameter ratio ranging from 5 to 100, an optical transmitter mounted to the antenna and disposed so as to be substantially in contact with a back of the at least one through hole of the antenna which is opposite to the opening of the a least one through hole provided on the side of the antenna facing the generated plasma, means for measuring a light from the sample passing through the at least one through hole by way of the optical transmitter, thereby detecting optical information showing a surface state of the sample, and means for judging the state of generation of obstacles in the processing chamber based on fluctuation of the optical information.

9. A plasma processing apparatus according to claim 7 or 8, further comprising means for informing a large fluctuation of the light from the sample.

10. A plasma processing apparatus according to claim 1, 4, 7 or 8, wherein a plurality of through-holes are provided.

11. A plasma processing apparatus according to claim 1 or 4, wherein a plurality of through-holes are provided, and a total of an area of openings of the through-holes ranges from 5% to 50% of a region of the conductive member which is covered by an end face of the optical transmitter.

* * * * *